US00PP23627P3

(12) United States Plant Patent
Korlipara

(10) Patent No.: US PP23,627 P3
(45) Date of Patent: May 21, 2013

(54) ***ECHINACEA* PLANT NAMED 'SECRET JOY'**

(50) Latin Name: ***Echinacea* hybrid**
Varietal Denomination: Secret Joy

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 109 days.

(21) Appl. No.: 13/200,421

(22) Filed: Sep. 23, 2011

(65) Prior Publication Data

US 2013/0081179 P1 Mar. 28, 2013

(51) Int. Cl.
*A01H 5/00* (2006.01)

(52) U.S. Cl.
USPC ..... Plt./428

(58) Field of Classification Search ..... Plt./428
See application file for complete search history.

*Primary Examiner* — June Hwu

(74) *Attorney, Agent, or Firm* — Klarquist Sparkman, LLP

(57) ABSTRACT

A new and distinct *Echinacea* plant named 'Secret Joy' characterized by large inflorescences with light cream colored ray florets, dark cream colored enlarged disc florets forming an anemone-type inflorescence, and good vigor.

1 Drawing Sheet

Botanical denomination: *Echinacea* hybrid.

Variety designation: 'Secret Joy'.

The present invention relates to a new and distinct cultivar of *Echinacea* and given the cultivar name 'Secret Joy'. *Echinacea* is in the family Asteraceae. This new cultivar is a third generation seeding originating from a planned breeding program using *Echinacea purpurea* 'Razzmatazz' (U.S. Plant Pat. 13,894) as the seed parent in the original cross and unnamed proprietary, unreleased interspecific hybrids (*Echinacea paradoxa*×*Echinacea purpurea*) for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety has a more compact habit and larger inflorescences that are white rather than pink.

Compared to *Echinacea* 'Meringue' (U.S. Plant Pat. No. 20,537), the new cultivar is taller with larger inflorescences and longer ray florets that are cream rather than white.

SUMMARY OF THE INVENTION

This new *Echinacea* cultivar is distinguished by:

1. large inflorescences with light cream colored ray florets,
2. dark cream colored enlarged disc florets forming an anemone-type inflorescence, and
3. good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
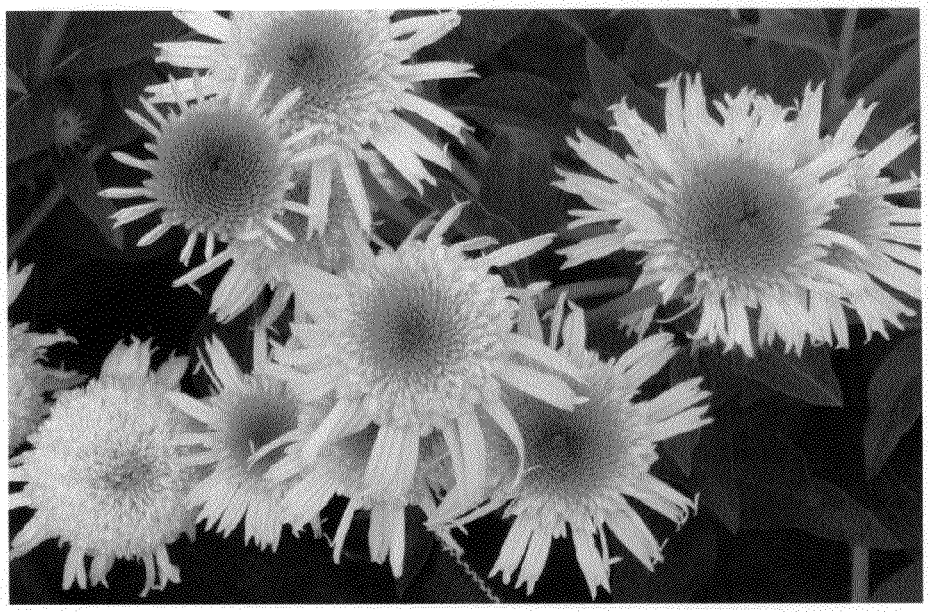
FIG. 1 shows the new flowers on a one-year-old *Echinacea* 'Secret Joy' growing in the field in full sun in July in Canby, Oreg.
Figure 2:
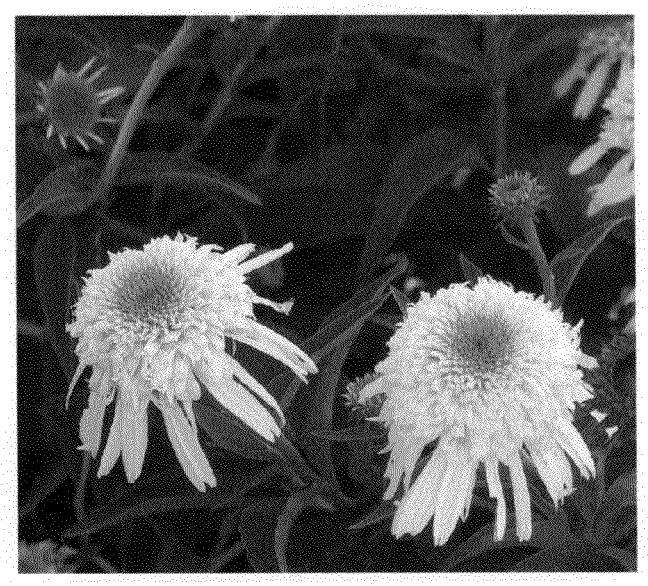
FIG. 2 shows the older flowers.

The following is a detailed description of the new *Echinacea* cultivar based on observations of 1-year-old specimens growing in the ground in the trial beds in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type*.—Herbaceous perennial.

*Hardiness*.—USDA Zones 4 to 9.

*Size*.—Grows to about 71 cm wide and 65 cm tall to top of inflorescences.

*Form*.—Basal clump, with about 5 stems from the base.

*Vigor*.—Excellent.

*Roots*.—Fibrous, with many downward growing and few laterals, ivory in color, Yellow White 158D, roots develop easily from cuttings from the crown.

Stem (flowering):

*Type*.—Ascending, with 2 to 5 flowering branches off the main flowering stems.

*Size*.—To 59 cm tall to a terminal inflorescence and 7 mm wide at base.

*Internode length*.—2 cm to 4 cm.

*Surface texture*.—Strigose.

*Color*.—Yellow Green N144D.

Leaf (basal):

*Type*.—Simple.

*Shape*.—Ovate to broadly lanceolate.

*Arrangement*.—Basal.

*Blade size*.—Grows to 13.5 cm long and 7 cm wide.
*Margins*.—Coarsely serrate.
*Apex*.—Acute.
*Base*.—Attenuate.
*Surface texture*.—Strigose on both sides.
*Venation*.—Pinnate.
*Color*.—Topside, Green 137A, bottom side closest to Yellow Green 147B with vein Yellow Green 145A.
*Petiole description*.—Grows to 16 cm long and 3 mm wide, strigose, Yellow Green 145A.

Leaf (stem):
*Type*.—Simple.
*Shape*.—Lanceolate to ovate.
*Arrangement*.—Alternate.
*Blade size*.—Grows to 10 cm long and 4.6 cm wide.
*Margins*.—Sparsely serrate, somewhat undulate.
*Apex*.—Acuminate.
*Base*.—Attenuate.
*Surface texture*.—Strigose on both sides.
*Venation*.—Pinnate, with 3 main veins from the base.
*Color*.—Topside, Green N137A with veins Yellow Green 147C, bottom side closest to Yellow Green 147B with veins Yellow Green 146B.
*Petiole description*.—On lowermost leaves only, clasping, grows to 2 cm long and 5 mm wide above the clasp, strigose, Yellow Green 146C.

Inflorescence:
*Type*.—Composite on terminal stalked heads.
*Number of flowering stems per plant*.—About 5.
*Flowering stem*.—Grows to 60 cm tall from the base of the plant to the terminal inflorescence and can grow to 17 cm long from the top stem leaf to the base of an inflorescence; branched, with 2 to 6 inflorescences per stem; diameter growing to 8 mm wide near the inflorescence; strigose; Yellow Green N144D.
*Size*.—Grows to 12 cm wide and 8 cm deep as disc enlarges.
*Form*.—Ray florets held horizontally when young, reflex down when mature, mature disc is conic.
*Phyllaries*.—In 4 leafy series, area 3.3 cm wide and 9 mm deep, lobes lanceolate in shape, grow to 10 mm long and 2 mm wide, Green 137A, margins strigose, tip acute, strigose on both sides.
*Receptacle*.—Grows to 16 mm wide and 18 mm deep, White 155A.
*Immature inflorescence*.—Grows to 3 cm wide and 2.5 cm deep, disc area 18 mm wide and Yellow Green 145A, ray florets held upright and rolled up so only the back color shows, Yellow Orange 16D.
*Ray florets*.—Without pistil or stamen, about 15 in number, grow to 60 mm long and 10 mm wide, oblanceolate with the tip two to three lobed (lobes ovate, 1 to 6 mm long and 2 to 4 nun wide, with acute tips), entire margins, base attenuate, glabrous on both sides; top and bottom side Yellow 13D.
*Disc*.—Flat becoming conic, becoming up to 55 mm deep and 60 mm wide with maturity, overall color when fully mature Yellow Orange 20B.
*Disc florets*.—About 130 in number, each with 1 pistil and 4 stamen, grow to 30 mm long and 8 mm wide, each with one persistent, very stiff linear bract (12 mm long with the top 3 mm colored Orange 24A then Yellow Green 144A, on bottom 9 mm); showy corollas grow to 26 mm long and 8 mm wide, tubular on the bottom with 5 lobes, spread out like a fan or fan-like in the middle and limb-like on the sides, glabrous on both sides, back side Yellow Orange 18D, inside color Yellow Orange 18B; pistil 12 mm long, ovary 3 mm long, White NN155D, style 6 mm long White 155A, 2-branched stigma spreading, Yellow Orange 18B; stamen 5 mm long, anthers 2 mm long and Greyed Orange 166A, filaments 3 mm long, White 155A, pollen Orange 23A.
*Bloom period*.—July through October in Canby, Oreg.
*Fragrance*.—Excellent, floral.
*Lastingness*.—Each inflorescence lasts about three weeks in Canby, Oreg.

Seeds: 0 to 3 per inflorescence, each 4 mm long and 2.5 mm wide, oval, Grey Brown N199A
*Fertility*.—Poor.

Disease and pests: No diseases or pests have been observed on plants grown under commercial conditions in Canby, Oreg. No resistances are known.

I claim:

1. A new and distinct *Echinacea* plant as herein illustrated and described.

* * * * *